(12) United States Patent
Feugier et al.

(10) Patent No.: US 11,497,785 B2
(45) Date of Patent: Nov. 15, 2022

(54) ORAL ANTI-PARASITIC COMPOSITION

(71) Applicant: Mars, Incorporated, McLean, VA (US)

(72) Inventors: Alexandre Feugier, Airmagues (FR); Nicolas Lerouxel, Airmagues (FR)

(73) Assignee: MARS, INCORPORATED, McLean, VA (US)

( * ) Notice: Subject to any disclaimer, the term of this patent is extended or adjusted under 35 U.S.C. 154(b) by 763 days.

(21) Appl. No.: 14/917,021

(22) PCT Filed: Sep. 5, 2014

(86) PCT No.: PCT/EP2014/068992
§ 371 (c)(1),
(2) Date: Mar. 6, 2016

(87) PCT Pub. No.: WO2015/032922
PCT Pub. Date: Mar. 12, 2015

(65) Prior Publication Data
US 2016/0206676 A1  Jul. 21, 2016

(30) Foreign Application Priority Data
Sep. 6, 2013  (EP) .................................. 13306227

(51) Int. Cl.
| A61K 36/61 | (2006.01) |
| A61K 9/00 | (2006.01) |
| A61K 36/53 | (2006.01) |
| A61K 36/54 | (2006.01) |
| A61K 36/23 | (2006.01) |
| A61K 31/7034 | (2006.01) |
| A61K 31/704 | (2006.01) |
| A61K 47/36 | (2006.01) |

(52) U.S. Cl.
CPC ............. *A61K 36/61* (2013.01); *A61K 9/0053* (2013.01); *A61K 31/704* (2013.01); *A61K 31/7034* (2013.01); *A61K 36/23* (2013.01); *A61K 36/53* (2013.01); *A61K 36/54* (2013.01); *A61K 47/36* (2013.01)

(58) Field of Classification Search
CPC ......... A61K 36/61; A61K 36/54; A61K 36/53
See application file for complete search history.

(56) References Cited

U.S. PATENT DOCUMENTS

| 4,197,319 | A | * | 4/1980 | Betz | ........................ | A23K 20/10 |
| | | | | | | 426/2 |
| 5,639,794 | A | | 6/1997 | Emerson et al. | | |
| 5,948,414 | A | | 9/1999 | Wiersma | | |
| 5,955,086 | A | | 9/1999 | DeLuca et al. | | |
| 6,197,305 | B1 | | 3/2001 | Friedman et al. | | |
| 6,322,825 | B1 | | 11/2001 | Ninkov | | |
| 6,569,843 | B1 | | 5/2003 | Walker | | |
| 6,623,767 | B1 | * | 9/2003 | Morice | .................... | A61P 31/04 |
| | | | | | | 424/745 |
| 6,800,294 | B1 | | 10/2004 | Ryan et al. | | |
| 6,872,713 | B1 | | 3/2005 | Maes et al. | | |
| 7,048,937 | B2 | | 5/2006 | Dawson et al. | | |
| 7,192,575 | B2 | | 3/2007 | Ryan et al. | | |
| 7,687,077 | B2 | | 3/2010 | Khoo et al. | | |
| 8,293,286 | B2 | | 10/2012 | Nouvel | | |
| 9,132,103 | B2 | | 9/2015 | Medepalli et al. | | |
| 9,271,486 | B2 | | 3/2016 | Messina | | |
| 10,398,748 | B2 | | 9/2019 | Pérez | | |
| 2005/0112179 | A1 | * | 5/2005 | Khoo | ..................... | A23K 10/30 |
| | | | | | | 424/442 |
| 2005/0112259 | A1 | * | 5/2005 | Qvyjt | ..................... | A23K 10/30 |
| | | | | | | 426/534 |
| 2005/0181072 | A1 | * | 8/2005 | Corthesy-Theulaz | ....................... | |
| | | | | | | A23F 3/163 |
| | | | | | | 424/725 |
| 2008/0118585 | A1 | | 5/2008 | Nouvel | | |
| 2008/0160000 | A1 | | 7/2008 | Motozono et al. | | |
| 2008/0171709 | A1 | | 7/2008 | Remmal | | |
| 2008/0171768 | A1 | | 7/2008 | Remmal | | |
| 2008/0193387 | A1 | | 8/2008 | Wolff | | |
| 2009/0285886 | A1 | | 11/2009 | Van Beek | | |

(Continued)

FOREIGN PATENT DOCUMENTS

| CN | 1190892 A | 8/1998 |
| CN | 1350435 A | 5/2002 |

(Continued)

OTHER PUBLICATIONS

Fayad et al. Innovative Systems Design and Engineering. vol. 4, No. 1, pp. 2222-2871. (Year: 2013).*
Khan et al. BMC Complementary and Alternative Medicine, 11:96, 16 pages. (Year: 2011).*
Becerril et al. "Evaluation of Bacterial Resistance to Essential Oils and Antibiotics After Exposure to Oregano and Cinnamon Essential Oils". Foodborne Pathogens and Disease 9(8):699-705 (Year: 2012).*
Leonova, "Aromatherapy for Beginners", Fair Press 2007 pp. 10-20.

(Continued)

*Primary Examiner* — Amy L Clark
(74) *Attorney, Agent, or Firm* — Morrison & Foerster LLP

(57) ABSTRACT

The present invention relates to a composition for use as an oral anti-parasitic, the composition comprises one or more of an essential oil which contains gamma-terpinene, and/or carvacrol, and/or thymol, and/or terpinenol, and/or eucalyptol and/or eugenol, an essential oil of genus *Cinnamomum, Eugenia, Eucalyptus* or a source of saponin. It also relates to a method of preventing or treating parasitic infection in an animal, the method comprising orally administering to said animal a composition comprising one or more of an essential oil which contains gamma-terpinene, and/or carvacrol, and/or thymol, and/or terpinenol, and/or eucalyptol and/or eugenol, an essential oil of genus *Cinnamomum, Eugenia, Eucalyptus* or a source of saponin.

11 Claims, 5 Drawing Sheets

(56) References Cited

U.S. PATENT DOCUMENTS

Figures 2A, 2B:
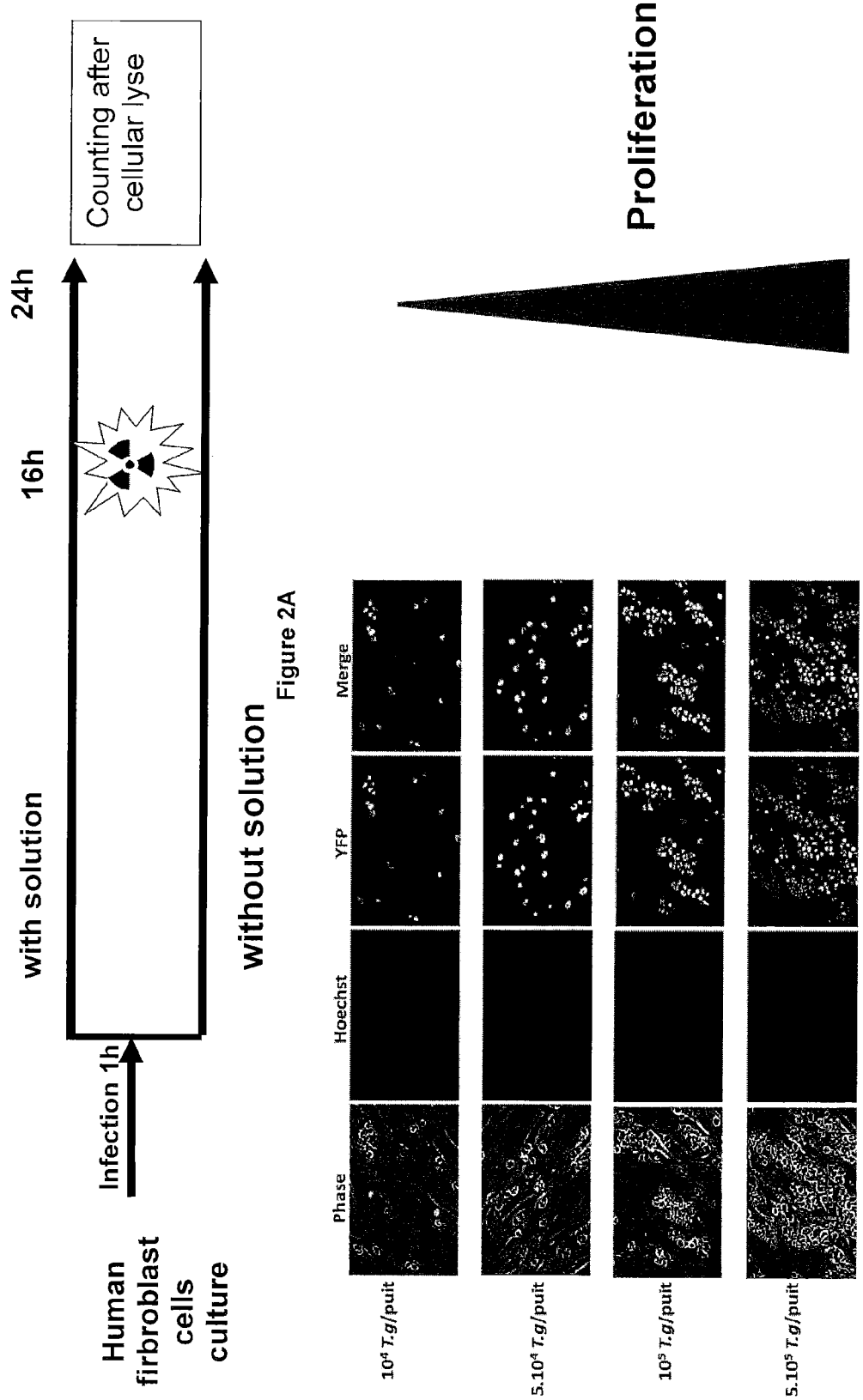

| | | | |
|---|---|---|---|
| 2010/0240768 A1 | 9/2010 | Fowler et al. | |
| 2011/0008471 A1 | 1/2011 | Ean | |
| 2011/0008474 A1 | 1/2011 | Boegli | |
| 2011/0268780 A1 | 11/2011 | Markus et al. | |
| 2012/0276024 A1 | 11/2012 | Albert | |
| 2012/0282356 A1* | 11/2012 | Schrader | A23L 3/3508 424/732 |
| 2013/0156835 A1 | 6/2013 | Sardo | |
| 2014/0037698 A1 | 2/2014 | Pablos Perez | |
| 2014/0045692 A1 | 2/2014 | Rossines et al. | |
| 2014/0106012 A1 | 4/2014 | Levin et al. | |
| 2014/0220164 A1 | 8/2014 | Manhas et al. | |

FOREIGN PATENT DOCUMENTS

| | | |
|---|---|---|
| CN | 1521182 A | 8/2004 |
| CN | 1331601 C | 8/2007 |
| CN | 101919852 A | 12/2010 |
| CN | 102274177 A | 12/2011 |
| CN | 102397379 A | 4/2012 |
| CN | 103037881 B | 12/2016 |
| DE | 3025223 | 1/1981 |
| DE | 10306987 A1 | 9/2004 |
| EP | 0116401 | 8/1984 |
| GB | 2114439 A | 8/1983 |
| JP | H0746963 | 2/1995 |
| JP | 2001247424 A | 9/2001 |
| JP | 2006306777 | 11/2006 |
| WO | 93/37210 A3 | 2/1997 |
| WO | 99/34811 A1 | 7/1999 |
| WO | 99/65505 A1 | 12/1999 |
| WO | 01/08496 A1 | 2/2001 |
| WO | 2005074965 A1 | 8/2005 |
| WO | 2008/048963 A2 | 4/2008 |
| WO | 2012/098282 A1 | 7/2012 |
| WO | 2012/114201 A1 | 8/2012 |
| WO | 2012/176131 A1 | 12/2012 |
| WO | 2013/050967 A1 | 4/2013 |
| WO | 2013/070441 A1 | 5/2013 |
| WO | 2015/032922 A1 | 3/2015 |

OTHER PUBLICATIONS

"A Balanced Diet", Waltham Book of Dog and Cat Nutrition, Ed ATB, Edney, Chapter by A. Rainbird, pp. 57-74, Pergamon Press, Oxford, 1988., 1988.
Bakkali, et al., "Biological effects of essential oils—A review", Food and Chemical Toxicology, 46., Sep. 21, 2007, 446-475.
Dahbi, et al., "The Effect of Essential Oils from Thymus broussonetii Boiss on Transmission of Toxoplasma gondii Cysts in Mice", Parasitol Res., 107, 2010, 55-58.
Pillai, et al., "Anti-parasitic activity of myristica fragrans houtt. Essential oil toxoplasma gondii parasite", APCBEE Procedia 2, Apr. 7, 2012, 92-96.
Sparg, et al., "Biological activities and distributing of plant saponins", Journal of Ethnopharmacology vol. 94, No. 2-3, Oct. 1, 2004, 219-243.
Li, et al., "Experimental Studies on the Volatile Oil from Eucalyptus globulus against Some Parasite", Journal of Guiyang Medical College, vol. 25, No. 4, Dec. 31, 2000, pp. 362-364 (English Abstract).
Calsamiglia, et al., "The use of essential oils in ruminants as modifiers of rumen microbial fermentation", Penn State Dairy Cattle Nutrition Workshop, Nov. 13-14, 2007, p. 87-100.
Abbas, et al., "Botanicals: an alternative approach for the control of avian coccidiosis," World's Poultry Science Journal, Jun. 2012, vol. 68, pp. 203-215.
Gustavo, Haralampidou da Costa Vieira, et al., "Use of essential oils to control Varroa destructor mite in Apis mellifera," Tropical Farming Research, 2012, vol. 42, No. 3, 6 pages (online journal).
Liu, Meng, et al., "Recent Advance of the Plant Essential Oil," China Animal Husbandry & Veterinary Medicine vol. 36, No. 6, pp. 252-254. Jun. 2011.
Monzote, L., et al., "Antiprotozoal Activity of Essential Oils," Agriculturae Conspectus Scientificus, 2012, vol. 77, No. 4, pp. 167-175.
Asaro et al. (2018). "Modelling net energy of commercial cat diets", located at https://atrium.lib.uoguelph.ca/xmlui/handle/10214/12926?show=full; (24 pages).
Behnia et al. (Sep. 2008). "Inhibitory Effects of Iranian Thymus vulgaris Extracts on in Vitro Growth of Entamoeba histolytica" Korean J. Parasitol 46 (3): 153-156.
Fei et al. (2011) "Antibacterial Effects of Cinnamon Oil Combined wtih Thyme or Clove Oil" Agricultural Sciences in China Science Direct 10(9):1482-1487.
Giannenas et al. (Apr. 2003). "Effect of Dietary Supplementation with Oregano Essential oil on Performance of Broilers After Experimental Infection with Eimeria Tenella" Arch.Anim.Nutr. 57(2):99-106.
Machado et al. (2011). "Anti-Giardia activity of Syzygium armaticum essential oil and eugenal: Effects on growth, viability, adherence and ultrastructure" Experimental Parasitology 127(2011):732-739.
Santoro et al. (2007). "Trypanosoma cruzi: Activity of essential oils from *Achillea millefolium* L., *Syzygium aromaticum* L. and *Ocimum basilicum* L. on epimastigotes and trypomastigotes" Experimental Parasitology ScienceDirect 116 (2007):283-290.

* cited by examiner

Figure 1

A

| EO Cinnamon China (leaves) *Cinnamomum cassia* | % |
|---|---|
| Cinnamaldehyde | 70-90 |
| o-Methoxycinnamaldehyde | <10 |
| Cinnamyl acetate | <5 |
| Coumarin | <5 |
| Phenylethyl alcohol | <5 |
| Benzaldehyde | <5 |
| Cinnamic acid | <5 |
| Salicylaldehyde | <5 |
| Cinnamyl alcohol | <5 |
| Styrene | <5 |
| Acetophenone | <5 |
| Eugenol | <5 |

B

| EO Clove Madagascar (leaves) *Eugenia caryophyllus* | % |
|---|---|
| Eugenol | 75-85 |
| beta-Caryophyllene | <15 |
| Eugenyl acetate | <5 |
| Methyl eugenol | <5 |

C

| EO Winter savory Balkans (leaves) *Satureja montana* | % |
|---|---|
| Carvacrol | 40-60 |
| p-Cymene | <20 |
| gamma-Terpinene | <10 |
| Linalool | <10 |
| Thymol | <5 |
| Myrcene | <5 |
| beta-Caryophyllene | <5 |
| alpha-Pinene | <5 |
| alpha-Terpinene | <5 |
| Terpinene 1 of 4 | <5 |
| alpha-Thuyene | <5 |
| beta-Pinene | <5 |

D

| EO Red Thyme Spain (leaves) *Thymus zygis* | % |
|---|---|
| Thymol | 40-60 |
| p-Cymene | <20 |
| gamma-Terpinene | <15 |
| Linalool | <5 |
| Carvacrol | <5 |
| beta-Caryophyllene | <5 |
| Myrcene | <5 |
| Terpinene 1 of 4 | <5 |
| alpha-Terpinene | <5 |
| alpha-Pinene | <5 |
| alpha-Thuyene | <5 |
| Methyl carvacrol ether | <5 |
| Limonene | <5 |
| trans-Hydrate Sabinene | <5 |

E

| EO Origano (leaves) *Origanum vulgare* | % |
|---|---|
| Carvacrol | 65-85 |
| gamma-Terpinene | <5 |
| p-Cymene | <5 |
| beta-Caryophyllene | <5 |
| Linalool | <5 |
| Thymol | <5 |
| Beta phellandrène+limonè | <5 |
| beta-Pinene | <5 |
| Borneol | <5 |
| Camphor | <5 |
| Terpinene 1 of 4 | <5 |
| alpha-Terpineol | <5 |
| alpha-Humulene | <5 |
| alpha-Terpinene | <5 |

F

| EO Eucalyptus China (leaves) *Eucalyptus globalus* | % |
|---|---|
| Eucalyptol | 70-90 |
| Limonene | <10 |
| gamma-Terpinene | <10 |
| p-Cymene | <5 |
| alpha-Pinene | <5 |

G

| EO Australian Tea Tree (leaves) *Melaleuca alternifolia* | % |
|---|---|
| 4-Terpinenal | 70-90 |
| gamma-Terpinene | <10 |
| alpha-Terpinene | <10 |
| alpha-Terpineol | <5 |
| Terpinolene | <5 |
| alpha-Pinene | <5 |
| Eucalyptol | <5 |
| p-Cymene | <5 |
| Limonene | <5 |
| delta-Cadinene | <5 |
| Viridiflorol (Viridiflorol gamma) | <5 |
| Sabinene | <5 |
| beta-Pinene | <5 |

H

| Saponin sources *Yucca schidigera* | % |
|---|---|
| Diosgénine | 30-50 |
| sarsapogénine | 10-30 |
| smilagénine | <15 |
| tigonenine | <5 |
| hecogenine | <5 |
| 9-dehydrohecogenine | <5 |
| gitogenine | <5 |
| chlorogenine | <5 |
| yuccagenine | <5 |
| samogenine | <5 |
| manogenine | <5 |
| 9-dehydromanogenine | <5 |
| kammogenine | <5 |

ORAL ANTI-PARASITIC COMPOSITION

The present invention relates to a composition for use as an oral anti-parasitic, the composition comprises one or more of an essential oil which contains gamma-terpinene, and/or carvacrol, and/or thymol, and/or terpinenol, and/or eucalyptol and/or eugenol, an essential oil of genus *Cinnamomum, Eugenia, Eucalyptus* or a source of saponin. It also relates to a method of preventing or treating parasitic infection in an animal, the method comprising orally administering to said animal a composition comprising one or more of an essential oil which contains gamma-terpinene, and/or carvacrol, and/or thymol, and/or terpinenol, and/or eucalyptol and/or eugenol, an essential oil of genus *Cinnamomum, Eugenia, Eucalyptus* or a source of saponin.

Parasitic infection can affect all animals. In particular, dogs and cats are major hosts for parasites, at least 80% of dogs and cats are infected by a type of endoparasite. In breeding environments, between 20-30% of dogs and cats are particularly subject to some internal parasites, such as coccidians. Parasite infection can cause symptoms such as worm infestation, abdominal pain, bowel obstructions, diarrhea and vomiting eventually leading to dehydration, sleeping problems, anemia, aching muscles or joints, allergies and/or fatigue. In particular, cats and dogs are hosts to many parasites and thus close contact can lead to increasing risks of parasite infection to humans (zoonosis).

Plant extracts have been used in combination with chemical drugs, in particular for applying on the skin of the animals as spot on anti-parasitic medicines, for example EP0116401. The problem with these spot-on methods is that the skin of the animal becomes irritated and can cause skin damage.

There is thus a need to develop further alternative medicines and/or foodstuffs for animals to reduce parasite infection, in particular endoparasites in dogs and/or cats to reduce further increasing risks of zoonosis.

The present invention provides a composition that addresses this need.

The present invention provides a composition comprising one or more of an essential oil which contains gamma-terpinene, and/or carvacrol, and/or thymol, and/or terpinenol, and/or eucalyptol and/or eugenol, an essential oil of genus *Cinnamomum, Eugenia, Eucalyptus* or a source of saponin for use orally as anti-parasitic in animals. The composition of the present invention has shown to be effective in reducing parasite infection in animals.

Further, the composition of the invention has shown a beneficial effect when comprising two or more of an essential oil which contains gamma-terpinene, and/or carvacrol, and/or thymol, and/or terpinenol, and/or eucalyptol and/or eugenol, an essential oil of genus *Cinnamomum, Eugenia, Eucalyptus* or a source of saponin. The effect may be synergistic.

The present invention relates, for all aspects, to any animal, including a human. In particular, the present invention relates to a companion animal such as a dog or a cat.

The first aspect of this invention relates to a composition for use as an oral anti-parasitic, the composition comprising one or more of an essential oil which contains gamma-terpinene, and/or carvacrol, and/or thymol, and/or terpinenol, and/or eucalyptol and/or eugenol, an essential oil from genus *Cinnamomum, Eugenia, Eucalyptus* or a source of saponin.

Use as an anti-parasitic includes treating and/or preventing the symptoms of parasitic infection. Treating includes ameliorating the symptoms of parasitic infection.

The composition of the present invention can be used against parasites, in particular belonging to the phylum Apicomplexa. Apicomplexa is a large group of unicellular protists. This group of protists include organisms classified as coccidian, gregarines, piroplasms, haemogregarines and plasmodia. Preferably, the parasite is from the class conoidasida.

The composition of the invention can be used against parasites from the class conoidasida. Conoidasida includes two subclasses coccidia or gregarinia. Preferably, the parasite is from the subclass coccidia.

The composition of the present invention can be for use to treat coccidiosis. Preferably, the composition treats parasite infection against parasites from the genus *Isospora, Neospora* or *Toxoplasma*. Most preferably, the composition of the present invention can treat coccidiosis against the parasite species *Neospora caninum* or *Toxoplasma gondii*.

The composition of the present invention comprises one or more of an essential oil which contains gamma-terpinene.

Terpinenes are a group of isomeric hydrocarbons classified as terpenes that are naturally found in plants and flowers. Terpinenes have the molecular formula $C_{10}H_{16}$ and differ from one another in the position of the carbon double bonds. Terpinenes include ($\alpha$) alpha-terpinene, ($\beta$) beta-terpinene, ($\gamma$) gamma-terpinene or ($\delta$) delta-terpinene, in particular gamma-terpinene.

Essential oils are volatile mixture of esters, aldehydes, alcohols, ketones, terpenes, monoterpenes, sesquiterpenes, phenols and oxides, which can be prepared from any of the parts of the plant. Methods for extracting essential oils from plants, for example distillation or solvent extraction, are readily known in the art.

Essential oils can be extracted from any parts of the plants, such as from the leaves, flowers, stems, bark, seeds or roots. Preferably, the essential oil is extracted from the leaves.

Essential oils containing gamma-terpinene, and/or carvacrol, and/or thymol, and/or terpinenol, and/or eucalyptol and/or eugenol include the genus *Satureja, Thymus, Trachyspermum, Origanum* or *Melaleuca*. Compounds can also be synthetic, or isolated from natural sources. Mix of compounds from natural or synthetic sources can be used.

In particular, winter savory oil can be obtained from the leaves of *Satureja montana*, thyme oil can be obtained from the leaves of *Thymus vulgaris* or *Thymus zygis*, oregano oil can be obtained from the leaves of *Origanum vulgare*.

The essential oil containing gamma-terpinene can be of any of the genus *Satureja, Thymus, Trachyspermum, Origanum* or *Melaleuca*.

The composition of the present invention comprises one or more of an essential oil of genus *Cinnamomum, Eugenia, Eucalyptus*.

The essential oil of genus *Cinnamomum* can be cinnamon. The essential oil of genus *Eugenia* can be clove. The essential oil of genus *Eucalyptus* can be *eucalyptus*. Preferably, the essential oil is cinnamon.

Cinnamon is a spice that is obtained from the inner bark of *Cinnamomum* trees. Cinnamon includes *Cinnamomum verum, Cinnamomum burmanii, Cinnamomum loureuros* or *Cinnamomum cassia*. Preferably, the cinnamon oil is extracted from *Cinnamomum cassia* (also called Chinese cassia). Most preferably, the cinnamon oil is extracted from the leaves of *Cinnamomum cassi*.

Clove is a spice that is obtained from the flower buds of a tree in the family of Myrtaceae. In particular, the clove oil is extracted from the flower buds of *Syzygium aromaticum*. Preferably, the clove is *Eugenia caryophyllus*.

*Eucalyptus* is a genus of flowering trees and shrubs in the family of Myrtaceae with over 700 species. In particular, the eucalyptus oil is extracted from *Eucalyptus globulus*. Preferably, the eucalyptus oil is extracted from the leaves of *Eucalyptus globulus*.

Saponins are chemical compounds naturally found in various plants and may also be found in marine organisms. Saponins can be found in the botanical families of Quillajaceae, Caryophyllaceae, Sapindaceae, Aceraceae, Hippocastanceae, Cucurbitancae, Araliaceae or Asparagaceae.

Preferably, a source of saponin is derived from the family of Asparagaceae. In particular, the source of saponin is derived from the genus *Yucca*. Most preferably, the source of saponin is derived from the species *Yucca schidigera*.

The source of saponin can be found in various parts of the plant such as: leaves, stems, roots, bulbs, blossom and fruit. Methods of extracting the source of saponin from plants are known.

Saponins are amphipathic glycosides composed of one or more hydrophilic glycoside moieties combined with a triterpene derivative. The number of saccharide chains attached can vary in length from 1 to 11, preferably from 2 to 5. The saccharide chains can be linear and/or branched.

The source of saponin can be steroidal.

Preferably, the saponin is a steroid sapogenin like diosgenine, sarsapogenine, smilagenine, tigonenine, hecogenine, 9-dehydrohecogenine, gitogenine, chlorogenine, yuccagenine, samogenine, manogenine, 9-dehydromanogenine or kammogenine.

A preferred composition includes one or more of an essential oil containing gamma-terpinene and one or more of an essential oil of cinnamon, clove or eucalyptus. Preferably, the composition contains oregano as the essential oil containing gamma-terpinene. Most preferably, the composition includes essential oils of oregano and cinnamon or oregano and clove.

The composition of the invention is any composition which an animal may consume or may consume as part of its diet.

The composition can be a liquid, a tablet or a foodstuff. Preferably, the composition can be a foodstuff. It can be any foodstuff, such as dry product, semi moist product, wet food product or a liquid and includes food supplement, a snack or a treat. Thus, the invention covers standard food products including liquids, as well as pet food snacks (for example, snack bars, pet chew, crunchy treat, cereal bars, snacks, biscuits and sweet products) and supplements.

The composition may be incorporated in a gelatinised starch matrix, or in any dry or wet foodstuffs or supplements. Methods of incorporation are known in the art.

The foodstuff is preferably a commercial pet product. Such a product is preferably sold as a product for feeding/administering to a pet animal, in particular a pet cat or a pet dog.

A typical dry pet foodstuff contains about 10-40% crude protein and about 5-40% fat, the remainder being carbohydrate, including dietary fibre and ash. A typical wet or moist product contains (on a dry matter basis) about 40% fat, 50% protein and the remainder being fibre and ash. The foodstuff of the invention may be a dry product (with approximately 5 to approximately 15% moisture), a semi-moist product (with approximately 15 to approximately 70% moisture) or a wet product (with approximately 70 to approximately 90% moisture). The foodstuff of the invention is preferably produced as a dry product containing from approximately 5% to approximately 15% moisture. The preferred dry food is more preferably presented as a small biscuit—like kibbles.

The remaining components of the foodstuff are not essential to the invention and typical standard products can be included. The combined ingredients of the foodstuff according to the invention can provide all of the recommended vitamins and minerals for the particular animal in question (a complete and balanced food).

The foodstuff can be provided as a food supplement. The food supplement can be a powder, sauce, topping, biscuit, kibble, pocket or tablet that can be administered with or without an additional foodstuff. Where the food supplement is administered with an additional foodstuff, the food supplement can be administered sequentially simultaneously or separately. The food supplement may be mixed with the foodstuff, sprinkled over the foodstuff or served separately. Alternatively, the food supplement can be added to a liquid provided for drinking such as water or milk.

The foodstuff is preferably a cooked product. It may incorporate meat or animal derived material (such as beef, chicken, turkey, lamb, fish, blood plasma, marrow bone etc. or one or more thereof). The product alternatively may be meat free (preferably including a meat substitute such as soya, maize gluten or a soya product) in order to provide a protein source. The foodstuff may contain additional protein sources such as soya protein concentrate, milk proteins, gluten etc. The foodstuff may also contain a starch source such as one or more grains (e.g. wheat, corn, rice, oats, barley etc.), or may be starch free.

The foodstuff of the invention may be or may be used in combination with a complete and balanced food which provides all the recommended vitamins and minerals for the dog in questions, for example, as described in National Research Council, 1985, Nutritional Requirements for Dogs, National Academy Press, Washington D.C. (ISBN:0-309-03496-5); or Association of American Feed Control Officials, Official Publication 1996.

These values apply to a composition for feeding to an animal, in particular a companion animal, such as a dog or a cat.

The total amount of essential oil/saponin is from 0.01 to 1000 mg/kg (ppm) of foodstuff (solid or liquid).

The amount of essential oil/saponin can have a range of 0.01 to 500 mg/kg (ppm) 0.01 to 100 mg/kg (ppm), 0.01 to 50 mg/kg (ppm), 0.01 to 1 mg/kg (ppm), 100 to 1000 mg/kg (ppm) 100 to 500 mg/kg (ppm) 50 to 100 mg/kg (ppm), or to 50 mg/kg (ppm) or any combination thereof of food stuff (sold liquid).

The second aspect of the invention relates to a method of preventing or treating parasitic infection in an animal.

The composition of the invention has demonstrated to provide, inter alia, a decrease in parasite infection and proliferation in vitro. The composition of the invention prevents and/or treats parasite infection in animals, including the prevention of zoonosis and prevention and/or treatment in a breeding kennel environment.

In particular, it is a desire in the area of pet foodstuff and companion animal health to provide foodstuff including supplements suitable to support the health of the companion animals. In particular, it is a desire to provide diets suitable to promote or maintain the health of already healthy companion animals as preventative diets.

In particular, the second aspect of the invention provides a method for preventing and/or treating parasitic infection in an animal, including ameliorating the symptoms of parasite infection. The method comprises administering to said animal a composition which comprises one or more of an essential oil which contains gamma-terpinene, gamma-terpinene, and/or carvacrol, and/or thymol, and/or terpinenol, and/or eucalyptol and/or eugenol, an essential oil of genus *Cinnamomum, Eugenia, Eucalyptus* or a source of saponin The animal may be in need thereof.

The present invention relates, for all aspects, to any animal, including a human. In particular the present invention relates to a companion animal such as a dog, a cat or any other such animal that suffers or is prone to suffer from parasite infection. Since a significant number of dogs and/or cats are hosts to parasites, thus are readily prone to parasitic infection.

In particular embodiments, the method comprises administering to said animal a composition comprising one or more of an essential oil which contains gamma-terpinene, and/or carvacrol, and/or thymol, and/or terpinenol, and/or eucalyptol and/or eugenol, an essential oil of genus *Cinnamomum, Eugenia, Eucalyptus* or a source of saponin. The composition can include one or more of an essential oil containing gamma-terpinene, and/or carvacrol, and/or thymol, and/or terpinenol, and/or eucalyptol and/or eugenol include the genus *Satureja, Thymus, Trachyspermum, Origanum* or *Melaleuca* and one or more of an essential oil of cinnamon, clove or *eucalyptus*. Preferably, the composition contains oregano as the essential oil containing gamma-terpinene and carvacrol. Most preferably, this composition includes essential oils of oregano and cinnamon or oregano and clove.

Further, the method is preferably administered to an animal, in particular a companion animal such as a dog and/or a cat, that suffers from parasite infection and is in need of ameliorating the symptoms of parasite infection or in need of preventing further symptoms of parasite infection. This may be to, for example a young pet animal, such as a puppy, or an older companion animal. Where the composition is a foodstuff, the foodstuff may be administered in a dietary regime in accordance with the usual dietary regime of the companion animal. The foodstuff may comprise 100% of the diet of the companion animal or a lesser proportion, depending on the level of prevention or treatment required. The foodstuff allows the composition to be administered with ease thus avoiding a need to supplement the companion animal's food. In addition, the foodstuff can be administered by the animal's owner thus avoiding constant veterinary supervision. The foodstuff may be available at any outlet selling pet food products or may be available from a veterinarian, or a breeder.

As used herein, the term "administration" also includes feeding or any other method of oral administration. Other means of administration may include tablets, capsules, injection, suppositories or any other suitable means.

Preferred features of the first aspect of the invention apply as for the second aspect of the invention mutatis mutandis.

In a third aspect of the invention there is provided a composition comprising two or more of the following essential oils from the genus *Cinnamomum, Eugenia, Satureja, Thymus, Trachyspermum, Orignum, Eucalyptus* or *Melaleuca*.

Preferably, the composition comprises an essential oil selected from winter savory, thyme, oregano or tea tree oil and an essential oil selected from cinnamon, clove or *eucalyptus*. Preferably, the composition contains oregano. Most preferably, the composition includes essential oils of oregano and cinnamon or oregano and clove.

Preferred features of the first and second aspect of the invention apply as for the third aspect of the invention mutatis mutandis.

In a fourth aspect of the invention there is provided a composition comprising a source of saponin and one or more of an essential oil which contains gamma-terpinene and/or carvacrol, and/or thymol, and/or terpinenol, and/or eucalyptol and/or eugenol, or an essential oil of genus *Cinnamomum, Eugenia* or *Eucalyptus*.

Preferably, the composition can include one or more of an essential oil containing gamma-terpinene and one or more of an essential oil of cinnamon, clove or eucalyptus. Preferably, the composition contains oregano as the essential oil containing gamma-terpinene. Most preferably, this composition includes essential oils of oregano and cinnamon or oregano and clove.

Preferred features of the first, second and third aspect of the invention, apply as for the fourth aspect of the invention mutatis mutandis.

The present description includes a method for preparing the composition of the invention.

The composition can include suitable carriers which are known in the art, for example silica dioxide, maltodextrine, Arabic gum or aluminosilicate minerals. The composition can be incorporated in a gelatinised starch matrix.

The composition can be sprayed onto foodstuff, mixed in with foodstuff or incorporated into foodstuff in a gelatinised starch matrix. Methods of inclusion of the composition are known in the art.

The present description includes a method for preparing the foodstuff of the invention.

The foodstuff can be made according to any method known in the art such as in Waltham Book of Dog and Cat Nutrition, Ed. ATB Edney, Chapter by A. Rainbird, entitled "A Balanced Diet" in pages 57 to 74 Pergamon Press Oxford.

For example, a process for the manufacture of a foodstuff as defined herein comprises mixing together ingredients with the composition which comprises one or more of an essential oil which contains gamma-terpinene, an essential oil of cinnamon, clove, eucalyptus or a source of saponin and forming a foodstuff, in particular a pet foodstuff. Heating/cooking may be applied to any one or more of the ingredients prior to, during or following the mixing.

The importance of the present invention is the beneficial properties of one or more of the essential oils and/or a source of saponin. In particular, an effect which is more than the cumulative effect may be seen.

The combination of the essential oils and/or source of saponin in the composition of the present invention can provide a synergistic effect in terms of one or more of reducing parasite infection and/or proliferation, preventing parasite infection and/or proliferation, decreasing risks of zoonosis and treating parasite infection, in particular coccidiosis.

A further benefit is seen when an essential oil contain gamma-terpinene and an essential oil of cinnamon, clove or eucalyptus are combined in the composition. In particular, when the essential oil containing gamma-terpinene is winter savory, thyme, oregano or tea tree oil and the second essential oil is cinnamon, clove or eucalyptus. Preferably, the composition contains oregano. Most preferably, the composition includes the essential oils oregano and cinnamon or oregano and clove.

The invention will now be further described by way of reference to the following Examples and Figures, which are provided for the purpose of illustration only and are not to be construed as being limiting on the invention.

FIG. 1: shows the 7 solutions of essential oils and source of saponin used. Each solution has been labeled A through to H.

FIG. 2A: shows a schematic diagram of the proliferation protocol followed. FIG. 2B shows fluorescence microscopy of HFF cells infected by different parasitical inoculums of *Toxoplasma gondii*.

Figure 3:
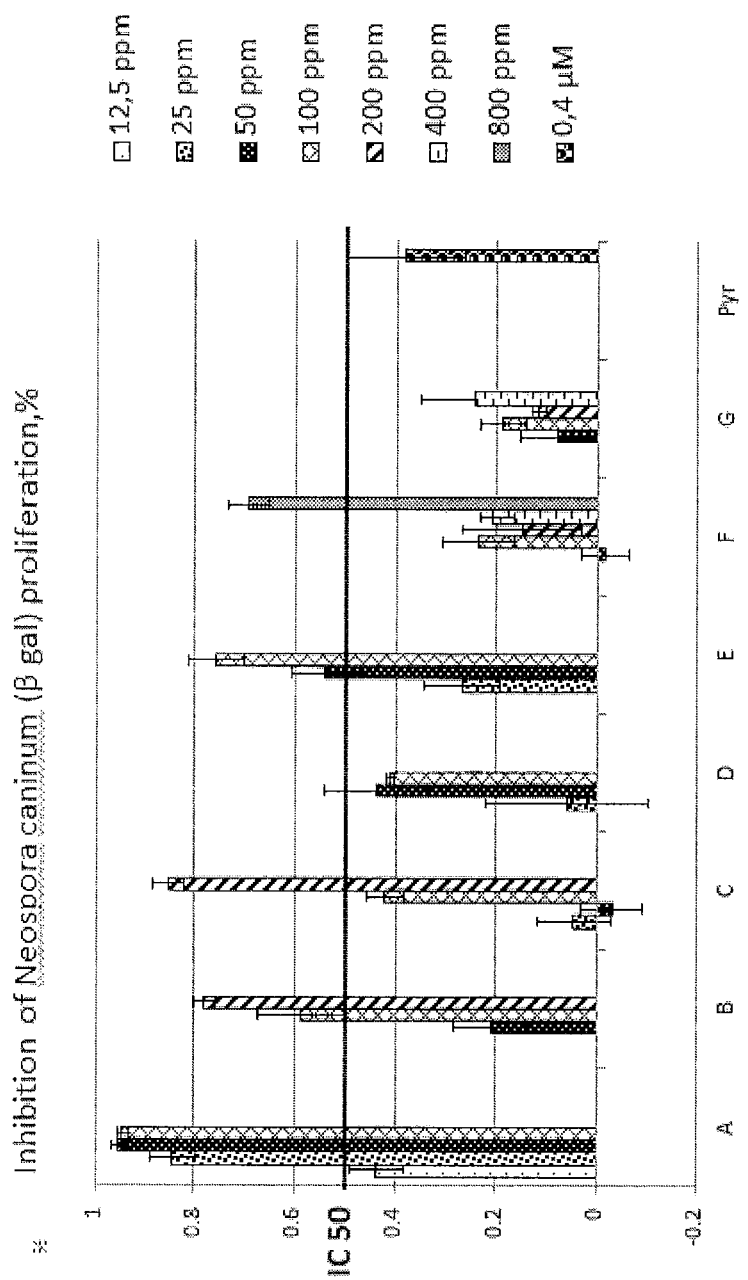

FIG. 3: shows results of a test of inhibition of the proliferation of *Neospora caninum* parasite in the presence of different essential oils at different concentrations. Summary of results and IC50 are set out in Table 1.

Figure 4:
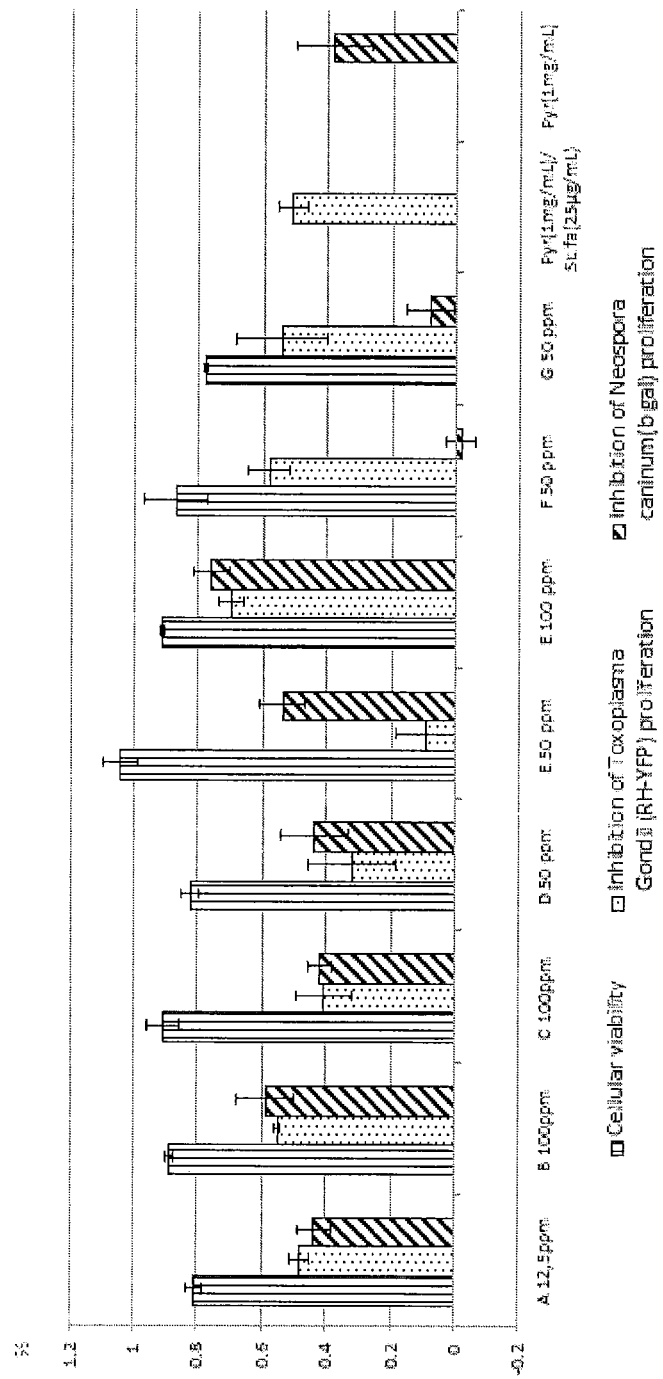

FIG. 4: shows comparative results of IC50 of 7 essential oils (oregano (E) tested at 50 ppm and 100 ppm) and the cell viability.

Figure 5:
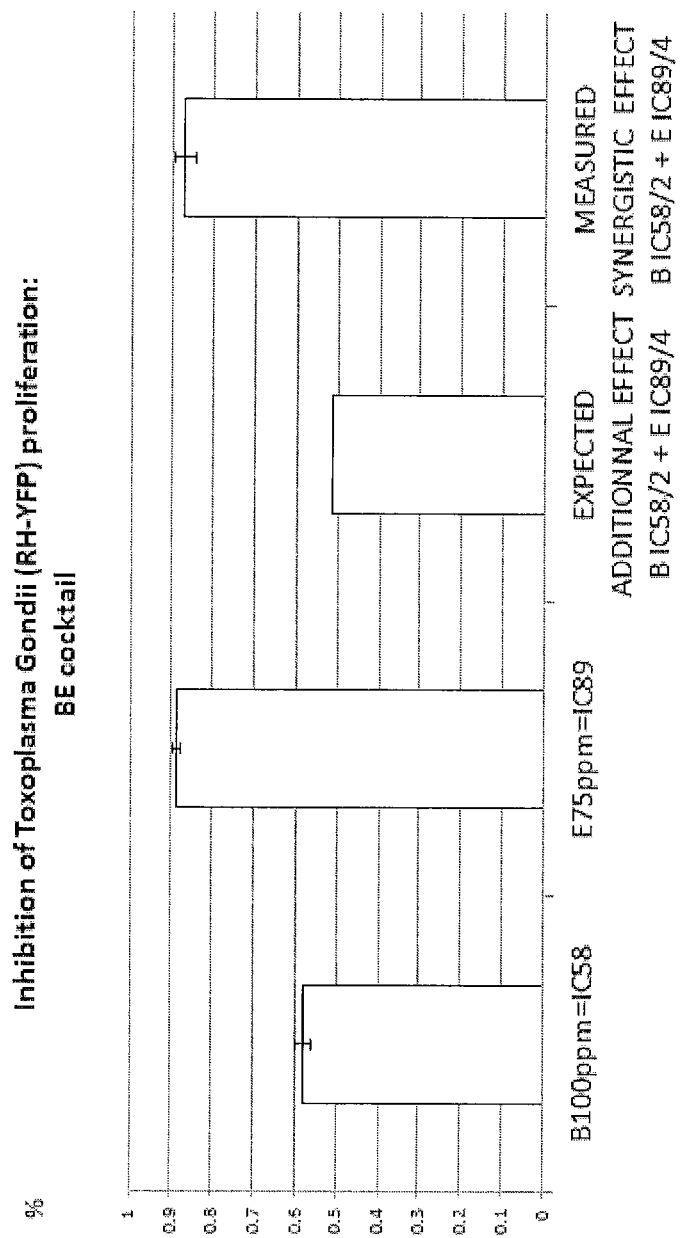

FIG. 5: shows results from a test of inhibition of proliferation of *Toxoplasma gondii* with a cocktail of essential oils EB (Oregano and Clove).

EXAMPLES

The study aimed to determine an anti-parasitic activity from seven essential oils on the intracellular microorganism *Neospora caninum*, but also combinations of these drugs on *Toxoplasma gondii*. The work focused on the capacity of proliferation of the parasite in the presence of these solutions containing the essential oils and invasion after pre-treatment.

Seven solutions of essential oils and one solution with a source of saponin were tested (see FIG. 1: A to H).

In order to solubilize the essential oils, the oils were diluted in dimethyl sulfoxide (DMSO) and then spread in the cell culture medium (DMEM) that was supplemented with 10% fetal calf serum (D10). DMSO was also used at a final concentration not exceeding 0.1%. Separate cultures of both parasites, *Toxoplasma gondii* and *Neospora caninum*, were prepared in vitro in human cell type HFF (Human Foreskin Fibroblasts), grown at 37° C. under 5% CO2 in a D10 medium. Both cultures were similar, the inoculum used for the various tests were the same, 105 parasites per well. It was observed that growing *Neospora caninum* is slower than that of *Toxoplasma gondii*.

Example 1: Proliferation Assay of *Neospora caninum* Parasite in the Presence of Essential Oils Proliferation of the parasite in the cells is measured by counting the specific radioactivity of the incorporated tritiated uracil and compared to the control without essential oil (100% proliferation). The test is performed in 24-well plates and the whole test lasts about 24 hours. The positive control is achieved using pyrimethamine (ICSO: 0.1 μg/mL). FIG. 3 shows ICSO of each essential oil solution tested at different concentrations in the presence of *Neospora caninum*.

Table 1 (below) summarises the results from example 1 in FIG. 3. Values represent inhibition of proliferation. The bracketed results show the ICSO of each essential oil tested.

| Essential Oil | 12.5 ppm | 25 ppm | 50 ppm | 100 ppm |
|---|---|---|---|---|
| A (Cinnamon) | [43.7%] | 84.3% | 95.3% | 94.5% |
| B (Clove) | | | 21.0% | [58.7%] |
| C (Winter savory) | | 4.6% | −3.1% | [42.2%] |
| D (Thyme) | | 6.0% | [43.8%] | 41.1% |
| E (Oregano) | | 26.7% | [53.9%] | 75.9% |
| F (Eucalyptus) | | | −1.6% | 23.9% |
| G (Tea tree) | | | 7.9% | 18.7% |

| Essential Oil | 200 ppm | 400 ppm | 800 ppm |
|---|---|---|---|
| A (Cinnamon) | | | |
| B (Clove) | 78.0% | | |
| C (Winter savory) | 85.2% | | |
| D (Thyme) | | | |
| E (Oregano) | | | |
| F (Eucalyptus) | 15.0% | 20.7% | 69.5% |
| G (Tea tree) | 11.6% | 24.5% | |

Example 2

The inhibition of proliferation was measured by incorporating tritiated uracil in both *Toxoplasma gondii* and *Neospora caninum* and the viability of HFF cells was assessed using MTT assay. The results are shown in FIG. 4.

FIG. 4 shows for each essential oil, having a concentration of proliferation inhibition properties for each of the parasites while maintaining cell viability HFF near 80%.

It can be observed that oils having a pesticidal activity, the IC50 concentrations obtained from *Toxoplasma gondii* are the same as for *Neospora caninum*. However, F and G oils have little or no action on the inhibition of the proliferation of *Neospora caninum*.

Example 3: Proliferation Assay of *Toxoplasma gondii* in the Presence of a Set of Combinations of Essential Oils The set of essential oils combinations are: AB, AE, AD and BE.

For each combination a 3 time 3 factorial design was drawn. The theoretical IC50 is adjusted to the measured inhibition proliferation rate and then is used as the basis to make dilutions and to make the subsequent 9 different ratios of the 2 essential oils combined in a cocktail.

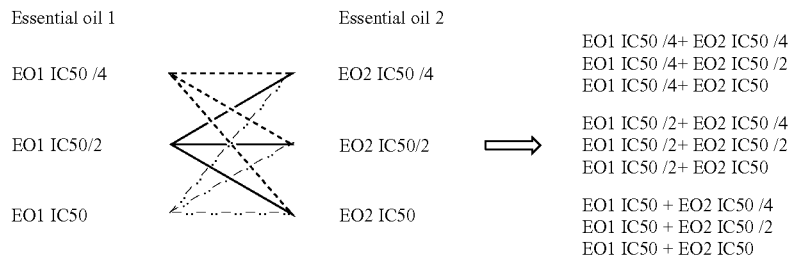

For each association, 9 tests of the inhibition of proliferation of *Toxoplasma gondii* were performed (all data not shown). Again, the inhibition of proliferation was measured by incorporation of tritiated uracil.

Cocktail BE (see FIG. 5): Shows the synergistic effect of cocktail BE on *Toxoplasma gondii* proliferation.

Essential oil B at 100 ppm alone corresponds to an IC58 (58% of proliferation inhibition). Essential oil E at 75 ppm alone corresponds to an IC88 (88% of proliferation inhibition). Assuming an independent relationship between the two oils on proliferation inhibition, a cocktail of essential oil B at IC58/2=IC29 with the essential oil E at IC88/4=IC22 leads to an expected additional effect of IC22+IC29=IC51 (51% of proliferation inhibition). The measured of proliferation inhibition of such a cocktail (B at IC22 combined to E at IC29) revealed a surprising measurable proliferation inhibition of 87% (IC87). This highly significant difference clearly highlights a synergistic effect of the cocktail BE on *Toxoplasma gondii* proliferation.

Bilan Cocktail

Table 2 (below) includes all the results on the inhibition of the proliferation of *Toxoplasma gondii* in the presence of the 36 batches of essential oils.

|    | IC 50/4<br>IC 50/4 | IC 50/4<br>IC 50/2 | IC 50/4<br>IC 50 | IC 50/2<br>IC 50/4 | IC 50/2<br>IC 50/2 |
|----|--------|--------|--------|--------|--------|
| AB | 16.4%  | 34.3%  | [63.5%] | 16.7%  | 39.3%  |
| AE | 45.5%  | [53.3%] | [85.7%] | 23.1%  | [53.5%] |
| BE | 27.7%  | [52.1%] | [79.6%] | [87.2%] | (93.4%) |
| AD | 19.4%  | 0.3%   | 31.9%  | [16.0%] | 20.2%  |

|    | IC 50/2<br>IC 50 | IC 50<br>IC 50/4 | IC50<br>IC 50/2 | IC 50<br>IC 50 |
|----|--------|--------|--------|--------|
| AB | [63.2%] | 47.6%  | [75.2%] | [82.4%] |
| AE | [86.0%] | [57.0%] | [67.0%] | (91.9%) |
| BE | [81.5%] | [73.8%] | [85.2%] | (96.4%) |
| AD | [53.5%] | [54.1%] | [60.0%] | [69.6%] |

Values represent inhibition of proliferation. Bracketed results show the combinations of inhibiting between 50-90% of the proliferation of the parasite. The results in parentheses shows those for inhibiting the proliferation of more than 90%.

CONCLUSION

Various tests on the two parasites have yielded highly similar results. The combination of essential oils has in some cases increased the capacity of inhibiting the proliferation of the compounds. This suggests that essential oils can act synergistically. This is particularly true for the combinations AE (data not shown) and BE, where the measured effect of the cocktail is significantly higher than the expected additional effect of both essential oil taken alone. It is also important to note that all items tested had no cytotoxic effects on HFF cells (monolayer integrity).

The invention claimed is:

1. A pet consumable comprising a single oral anti-parasitic composition, the single oral anti-parasitic composition consisting of a source of saponin, an essential oil of oregano and an essential oil from genus *Cinnamomum* or from genus *Eugenia*, wherein the essential oil of oregano and the essential oil from genus *Cinnamomum* or *Eugenia* are present in the anti-parasitic composition in a ratio of from 4:1 to 1:4, and wherein the anti-parasitic composition exhibits a greater proliferation inhibition with respect to *Neospora caninum* or *Toxoplasma gondii* than the combined proliferation inhibition of the individual components.

2. The pet consumable of claim 1, wherein the source of saponin contains a steroid sapogenin.

3. The pet consumable of claim 1, wherein the consumable is a foodstuff, and wherein the foodstuff comprises 70% to 90% moisture.

4. The pet consumable of claim 1, wherein the consumable is in the form of a liquid.

5. The pet consumable of claim 1, wherein the consumable is a foodstuff, and wherein the foodstuff comprises 5% to 15% moisture.

6. The pet consumable of claim 5, wherein the foodstuff comprises 10-40% protein or 5-40% fat.

7. The pet consumable of claim 6, wherein the foodstuff is in the form of a biscuit.

8. The pet consumable of claim 5, wherein the consumable is in the form of a tablet.

9. An anti-parasitic composition, consisting of an essential oil of oregano and an essential oil from genus *Cinnamomum* or genus *Eugenia*, and optionally, a source of saponin, wherein the essential oil of oregano and the essential oil from genus *Cinnamomum* or *Eugenia* are present in the anti-parasitic composition in a ratio of from 4:1 to 1:4, and wherein the anti-parasitic composition exhibits a greater proliferation inhibition with respect to *Neospora caninum* or *Toxoplasma gondii* than the combined proliferation inhibition of the individual components.

10. The pet consumable of claim 9, wherein the single oral parasitic composition consists of an essential oil of oregano and an essential oil from genus *Cinnamomum* or genus *Eugenia*.

11. A method of preventing or treating parasitic infection in an animal, the method comprising orally administering to said animal an anti-parasitic composition consisting of a source of saponin, an essential oil of oregano and an essential oil from genus *Cinnamomum*, or from genus *Eugenia*, wherein the essential oil of oregano and the essential oil from genus *Cinnamomum* or *Eugenia* are present in the anti-parasitic composition in a ratio of from 4:1 to 1:4 and wherein the composition exhibits a greater proliferation inhibition with respect to *Neospora caninum* or *Toxoplasma gondii* than the combined proliferation inhibition of the individual components.

* * * * *